United States Patent
Lampe et al.

(12) 
(10) Patent No.: US 6,444,707 B1
(45) Date of Patent: Sep. 3, 2002

(54) TOPICALLY APPLIED HOOF TREATMENT COMPOSITION AND CONCENTRATE

(75) Inventors: Joel Lampe, Lee's Summit; Thomas Hemling, Belton; Joycelyn L. Seymour, Kansas City, all of MO (US)

(73) Assignee: West Agro, Kansas City, MO (US)

( * ) Notice: Subject to any disclaimer, the term of this patent is extended or adjusted under 35 U.S.C. 154(b) by 0 days.

(21) Appl. No.: 09/643,707

(22) Filed: Aug. 22, 2000

(51) Int. Cl.⁷ .............................................. A61K 31/155
(52) U.S. Cl. ....................................... 514/642; 514/643
(58) Field of Search .................. 514/642, 643

(56) References Cited

U.S. PATENT DOCUMENTS

| | | | |
|---|---|---|---|
| 5,645,823 A | * 7/1997 | Thrall et al. | 424/61 |
| 5,780,064 A | 7/1998 | Meisters et al. | 424/616 |
| 6,028,104 A | 2/2000 | Schmidt et al. | 514/557 |

OTHER PUBLICATIONS

W.C. Rebhun et al., Interdigital Papillomatosis in Dairy Cattle, *JAVMA*, vol. 177, No. 5, pp. 437–440, Sep. 1, 1980.
USDA:APHIS:VS, Digital Dermatitis on U.S. Dairy Operations, NAHMS Dairy '96, 5/1997.

* cited by examiner

*Primary Examiner*—Kevin E. Weddington
(74) *Attorney, Agent, or Firm*—Hovey Williams LLP

(57) ABSTRACT

New aqueous concentrates adapted for dilution to form use compositions, and methods of preventing or treating hoof diseases with these use compositions are provided. The compositions and concentrates comprise (and preferably consist essentially of) a quaternary ammonium compound, an acid, and a surfactant. Preferred quaternary ammonium compounds include those selected from the group consisting of alkyl dimethyl benzyl ammonium salts, alkyl dimethyl ethyl benzyl ammonium salts, dialkyl dimethyl ammonium salts, dialkyl methyl benzyl ammonium salts, and mixtures thereof. The inventive methods comprise diluting the concentrate to form a use composition and applying the use compositions to the affected areas by spraying, under a bandage, or in a footbath. The invention is particularly well-suited for treating papillomatous digital dermatitis.

32 Claims, 6 Drawing Sheets

TOPICALLY APPLIED HOOF TREATMENT COMPOSITION AND CONCENTRATE

BACKGROUND OF THE INVENTION

1. Field of the Invention

The present invention is broadly concerned with new aqueous concentrates adapted for dilution to form use compositions and methods of using the diluted compositions to prevent or treat hoof diseases in animals. More particularly, the concentrates include a quaternary ammonium compound such as those selected from the group consisting of alkyl dimethyl benzyl ammonium salts, alkyl dimethyl ethyl benzyl ammonium salts, dialkyl dimethyl ammonium salts, dialkyl methyl benzyl ammonium salts, and mixtures thereof. The concentrates also include an acid and a surfactant.

2. Description of the Prior Art

Papillomatous digital dermatitis (PDD) or hairy hoof warts was first reported in 1974 and has since presented an increasing problem to dairy farms. As many as 47% of the dairy operations in the United States are affected by PDD, with the disease occurring in 40 or more states (see *Digital Dermatitis on U.S. Dairy Operations*, NAFMS Dairy '96 (1997), incorporated by reference herein). The etiology of PDD is unknown, although two to five spirochetes have been identified during the course of the disease.

The lesions first appear as eroded areas, usually between the heel bulbs. Ulcerative lesions are common in the early stages of the disease and are circumscribed with a red, granular (strawberry-like) surface. More mature lesions have a gray or yellowish-brown surface with tissue proliferations which grossly resemble hair. The lesions are very painful to the infected animal and can lead to a reduction in feed intake and a daily decrease in milk production of up to 50% in the affected cow (Rehbun et al., *Interdigital Papillomatosis in Dairy Cattle*, JAVMA, 137(5):437–40 (1980), incorporated by reference herein).

Various treatments have been attempted in order to prevent PDD and/or to promote healing of PDD lesions. For example, parenteral antibiotics have been administered to infected cattle, but this treatment requires milk withdrawal. Antibiotics have been applied topically (e.g., via spraying) to the affected area, but this treatment can cause the milk to be contaminated by the antibiotic. Additionally, there is concern that improper use of antibiotics will result in resistance of the disease to the antibiotic, thus making the disease even more difficult to treat. Furthermore, the antibiotic solutions are typically placed in a footbath through which the cattle walk after milking. However, because the antibiotic solutions are clear like water, there is a risk that the cattle will drink the solution, thus resulting in rumen damage.

Bandaging hooves with a topical treatment has been reported to be relatively effective, but it can be very labor-intensive and may not be practical for herds with a high incidence of the disease. Germicidal footbaths have also been utilized to apply a treatment solution to the affected area, but these footbaths are quickly overcome by the high organic loads to which they are subjected. As a result, the treatment solution must be replaced frequently, rendering the footbath a costly and labor-intensive method of treatment. Finally, many of these prior art treatment compositions or solutions contain copper as their active ingredient. While copper can be effective at treating the disease, it is also highly toxic to aquatic life. This is of particular concern because farmers typically wash farm waste into a lagoon, where the waste can seep into the soil and contaminate groundwater.

There is a need for effective and affordable treatments for treating hoof diseases in animals. This treatment should avoid the use of antibiotics, be effective for use as a spray or in a footbath in spite of the high level of contaminants which may be introduced into the footbath during use, and provide alternatives to the current copper-containing treatment solutions or compositions.

SUMMARY OF THE INVENTION

The present invention broadly provides aqueous concentrates adapted for dilution with water to form use compositions, and methods of using these compositions to treat hoof diseases such as PDD.

In more detail, the aqueous concentrates according to the invention comprise, and preferably consist essentially of, a quaternary ammonium compound, a surfactant, and an acid. Preferred quaternary ammonium compounds include those with biocidal properties, with particularly preferred such compounds being selected from the group consisting of alkyl (preferably $C_8$–$C_{20}$, and more preferably $C_{12}$–$C_{16}$) dimethyl benzyl ammonium salts, alkyl (preferably $C_8$–$C_{20}$, and more preferably $C_{12}$–$C_{18}$) dimethyl ethyl benzyl ammonium salts, dialkyl (preferably each alkyl group is individually selected from the group consisting of $C_8$–$C_{20}$ alkyl groups, and more preferably $C_8$–$C_{10}$ alkyl groups) dimethyl ammonium salts, dialkyl (preferably each alkyl group is individually selected from the group consisting of $C_8$–$C_{20}$ alkyl groups, and more preferably $C_{12}$–$C_{18}$ alkyl groups) methyl benzyl ammonium salts, and mixtures thereof. The most preferred quaternary ammonium compounds are selected from the group consisting of N-alkyl dimethyl benzyl ammonium chloride, octyl decyl dimethyl ammonium chloride, dioctyl dimethyl ammonium chloride, didecyl dimethyl ammonium chloride, and mixtures thereof.

The quaternary ammonium compound should be present in the concentrate at a level of from about 1–30% by weight, preferably from about 5–20% by weight, and more preferably from about 5–15% by weight, based upon the total weight of the concentrate taken as 100% by weight.

The surfactant should be present in the concentrate at a level of from about 1–30% by weight, preferably from about 1–20% by weight, and more preferably from about 5–20% by weight, based upon the total weight of the concentrate taken as 100% by weight. The surfactant is preferably a surfactant selected from the group consisting of amphoteric surfactants, nonionic surfactants, and mixtures thereof. Even more preferably, the concentrate includes at least one amphoteric surfactant and at least one nonionic surfactant. Preferred amphoteric surfactants include imidazolines and betaines. Preferred nonionic surfactants include alkyl (preferably $C_8$–$C_9$) phenol or alcohol ethoxylates, ethylene oxide propylene oxide adducts, and mixtures thereof. The alcohol ethoxylates are preferably $C_9$–$C_{13}$ linear primary alcohol ethoxylates and preferably comprise an average of from about 5–9 moles of ethylene oxide per mole of alcohol. One such surfactant is commercialized under the name NEODOL 1-7 ($C_{11}$ alcohol ethoxylate with 7 moles of ethylene oxide per mole of alcohol; available from Shell). The surfactant is particularly useful for providing stability to the composition, enhancing the detergency of the composition, and aiding in wetting the area to be treated.

The acid is preferably present in sufficient quantities to adjust the pH of the composition to less than about 4, preferably less than about 3, and more preferably less than about 2. This generally results in there being from about 0.5–15% by weight, preferably from about 0.5–10% by weight, and more preferably from about 1.0–10% by weight of the acid present in the concentrate. Preferred acids include glycolic acid, citric acid, lactic acid, phosphoric acid, hydrochloric acid, sulfuric acid, acetic acid, formic acid, nitric acid, and mixtures thereof.

It will be appreciated that optional ingredients can also be incorporated into the concentrates to alter certain properties thereof. For example, coloring agents (e.g., red or yellow dyes) can be added so that the use compositions formed from the concentrates can be visually observed when applied to the affected areas of the animal. Furthermore, the concentrates can include exfoliants (e.g., glycolic acid, salicylic acid), buffering agents (e.g., citric acid), and/or thickening or viscosity building agents (e.g., polyacrylic acids).

The concentrates are adapted for dilution with water to form aqueous use compositions, with the amount of the preferred dilutions depending upon the desired end use. That is, topical spray use compositions are preferably formed by mixing from about 0.5–25% by volume, and preferably from about 5–20% by volume of the concentrate with water to yield the use composition. Use compositions to be applied under a bandage wrap are preferably formed by mixing from about 0.5–25% by volume, and preferably from about 5–20% by volume of the concentrate with water to yield the use composition. Finally, use compositions to be used in a footbath are preferably formed by mixing from about 0.5–25% by volume, and preferably from about 0.5–20% by volume of the concentrate with water to yield the use composition.

Thus, use compositions formed from the inventive concentrates can be applied to the affected area by wiping or spraying the composition on the area. Alternately, a cloth or a piece of cotton or other absorbent material can be soaked in the composition and held against the lesions with a bandage wrap. When applied as a topical spray, the composition is preferably applied at least about 3 times per week. When applied under a bandage wrap, the wrap should remain on the affected area for at least about 24 hours. Finally, the compositions can be placed in a footbath, allowing the cattle to walk through the bath as they exit the milking facility. It will be appreciated that this allows for the composition to be used as a treatment for an infected hoof as well as a preventive measure to keep a healthy hoof free of disease.

DETAILED DESCRIPTION OF THE PREFERRED EMBODIMENTS

EXAMPLES

Figure 1:
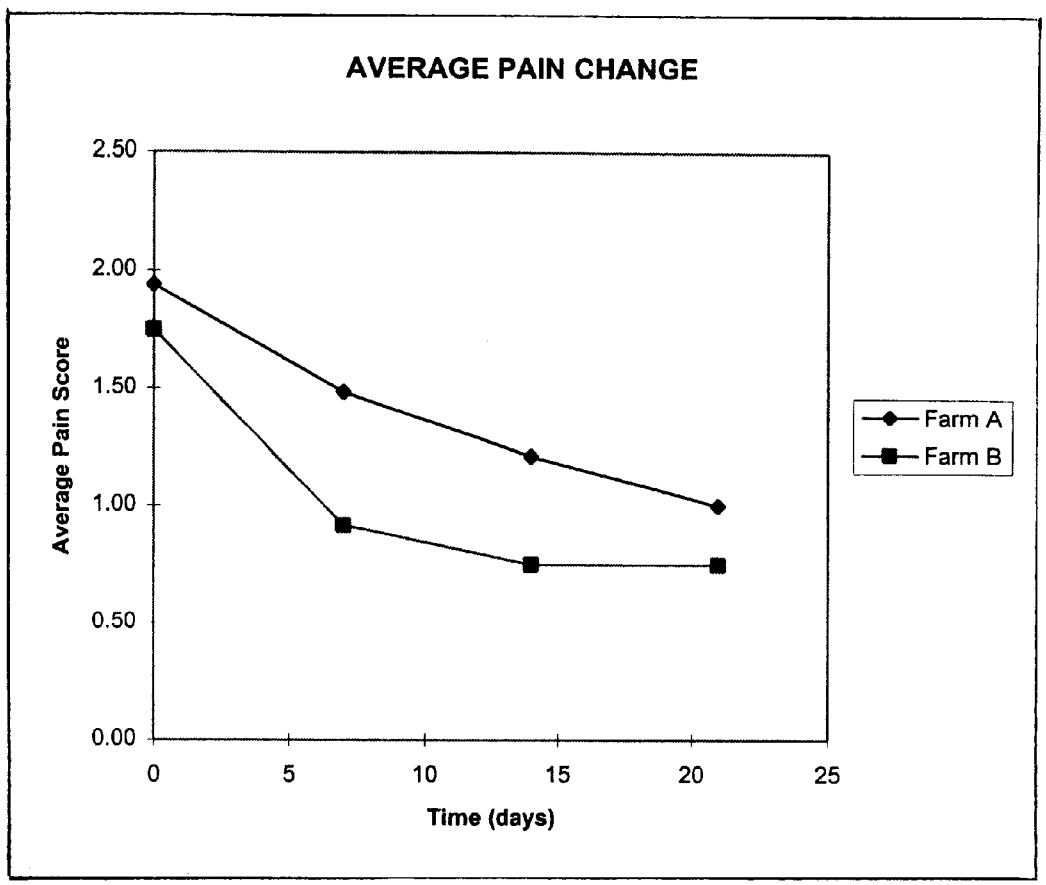
FIG. 1 is a graph depicting the change in average pain of PDD-infected cattle treated with a composition according to the invention.

The following examples set forth preferred methods in accordance with the invention. It is to be understood, however, that these examples are provided by way of illustration and nothing therein should be taken as a limitation upon the overall scope of the invention.

Example 1

A concentrate composition was prepared by mixing the ingredients in Table 1. Initially, the BARDAC 208M was mixed with 60% of the total water utilized and the remaining ingredients were added in the following order: NEODOL 1-7; MIRANOL C2M-SF; hydrochloric acid; the red and yellow dyes; and the remaining water.

TABLE 1

| Ingredients | % by weight[a] |
|---|---|
| water | 74.010% |
| BARDAC 208M[b] | 10.0% |
| NEODOL 1-7[c] | 12.000% |
| FD&C red no. 40[d] | 0.050% |
| FD&C yellow no. 6[d] | 0.160% |
| MIRANOL C2M-SF, concentrated[e] | 1.000% |
| hydrochloric acid, 37% | 2.780% |

[a] % by weight, based upon the total weight of the ingredients utilized taken as 100% by weight.
[b] obtained from Algroup Lonza, Fair Lawn, New Jersey - mixture of N,N-dialkyl-N,N-dimethyl-ammonium chloride (48% by weight); N-alkyl-N,N-dimethyl-N-benzylammonium chloride (32% by weight); ethyl alcohol (10% by weight); and water (10% by weight), with each % by weight being based upon the total weight of the mixture taken as 100% by weight.
[c] obtained from Shell - a $C_{11}$ alcohol ethoxylate with an average of 7 moles of ethylene oxide per mole of alcohol.
[d] dye obtained from Pylam Products.
[e] obtained from Rhône-Poulenc, Cranbury, New Jersey - cocoamphodipropionate (38% by weight); methanol (3.5% by weight); and water (58.5% by weight), with each % by weight being based upon the total weight of the ingredients utilized taken as 100% by weight.

Example 2

A concentrate composition was prepared by mixing the ingredients in Table 2. Initially, the BARDAC 208M was mixed with 60% of the total water utilized and the remaining ingredients were added in the following order: IGEPAL CO-630; sulfuric acid; the red and yellow dyes; and the remaining water.

TABLE 2

| Ingredients | % by weight[a] |
|---|---|
| water | 76.54% |
| BARDAC 208M | 10.0% |
| IGEPAL CO-630[b] | 12.000% |
| FD&C red no. 40 | 0.050% |
| FD&C yellow no. 6 | 0.160% |
| sulfuric acid, 50% | 1.25% |

[a] % by weight, based upon the total weight of the ingredients utilized taken as 100% by weight.
[b] obtained from Rhone-Poulenc - a nonylphenol ethoxylate with an average of 9 moles of ethylene oxide per mole of nonylphenol.

Example 3

A concentrate composition was prepared by mixing the ingredients in Table 3. Initially, the BTC 888 was mixed with 60% of the total water utilized and the remaining ingredients were added in the following order: NEODOL 91-6; Mafo 13; hydrochloric acid; the red and yellow dyes; and the remaining water.

TABLE 3

| Ingredients | % by weight[a] |
|---|---|
| water | 74.010% |
| BTC 888[b] | 10.0% |
| NEODOL 91-6[c] | 12.000% |
| FD&C red no. 40 | 0.050% |
| FD&C yellow no. 6 | 0.160% |
| Mafo 13[d] | 1.000% |
| hydrochloric acid, 37% | 2.780% |

[a]% by weight, based upon the total weight of the ingredients utilized taken as 100% by weight.
[b]obtained from Stepan - mixture of alkyl dimethyl benzyl and dialkyl dimethyl ammonium chlorides.
[c]obtained from Shell - a $C_9$–$C_{11}$ alcohol ethoxylate with an average of 6 moles of ethylene oxide per mole of alcohol.
[d]obtained from PPG Industries - an amphoteric surfactant.

Example 4

Field Trials

Twice a day for three weeks, the concentrate composition (12% by volume dilution with water) prepared in Example 1 was sprayed on the hooves of PDD-infected cattle from two different farms. The pain, lesion color, and lesion size on each animal was noted prior to treatment and recorded at various intervals after treatment. The lesion size was measured along the width of the lesion to the nearest ¼ cm with the size being recorded. The lesions were each assigned a number depending upon the color thereof. Table 4 indicates the number assigned to each color.

TABLE 4

| Lesion Color | Number Assigned |
|---|---|
| flesh-colored (indicating a healed lesion | 0 |

TABLE 4-continued

| Lesion Color | Number Assigned |
|---|---|
| black (a scabbed lesion) | 1 |
| gray | 2 |
| white | 3 |
| red (a raw, bleeding lesion) | 4 |

The pain was evaluated by spraying water on the lesion with a hose spray attachment from a distance of two feet. Prior to the actual measurement, both hind feet (or both front feet if the lesion was on a front foot) were initially sprayed with water to desensitize the animal to the water application after which the water was sprayed on the lesion to determine the pain measurements. If the animal did not flinch or raise the foot during spraying, the animal was considered to be in no demonstrable pain and was scored with a 0. If the animal flinched and/or raised a foot for less than two seconds, then the animal was considered to be in sensitive pain and was scored with a 1. Finally, if upon spraying the animal raised and held the foot off the ground for at least two seconds, then the animal was deemed to be in severe pain and was scored with a 2.

Figure 2:
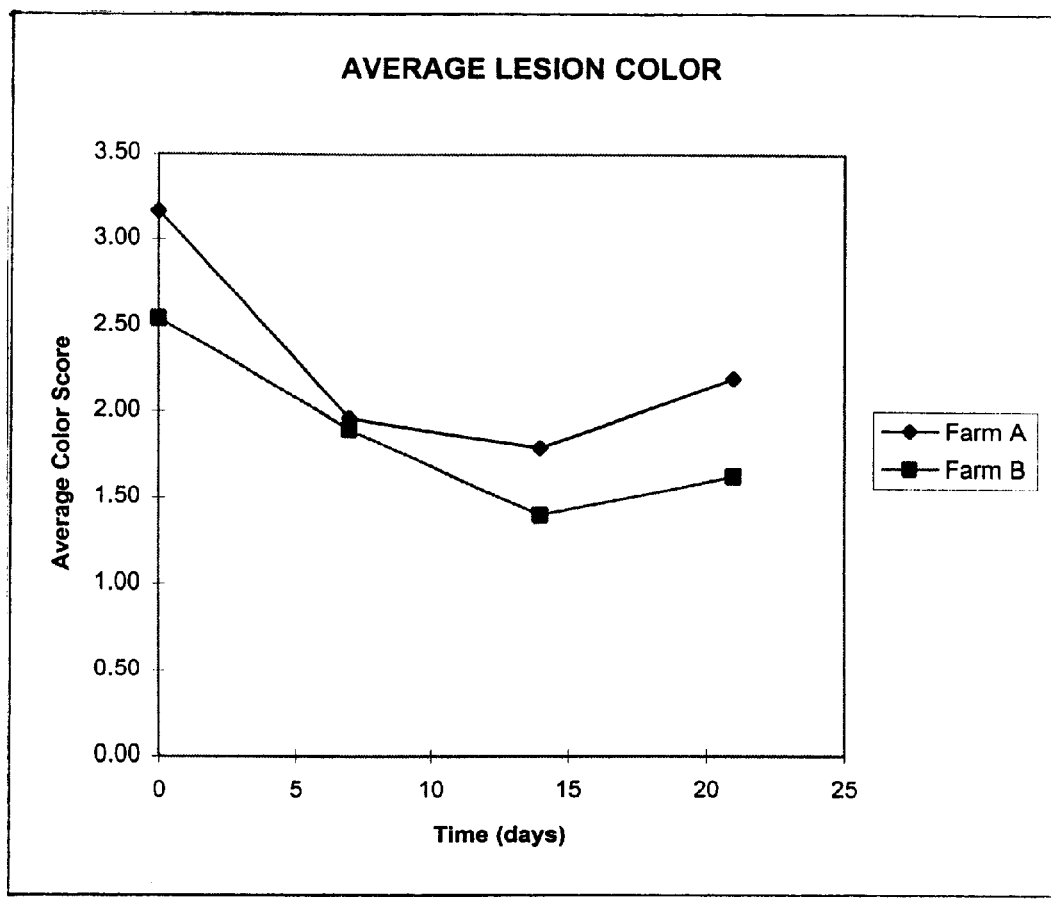
FIG. 2 is a graph depicting the change in color of lesions on PDD-infected cattle treated with a composition according to the invention.
Figure 3:
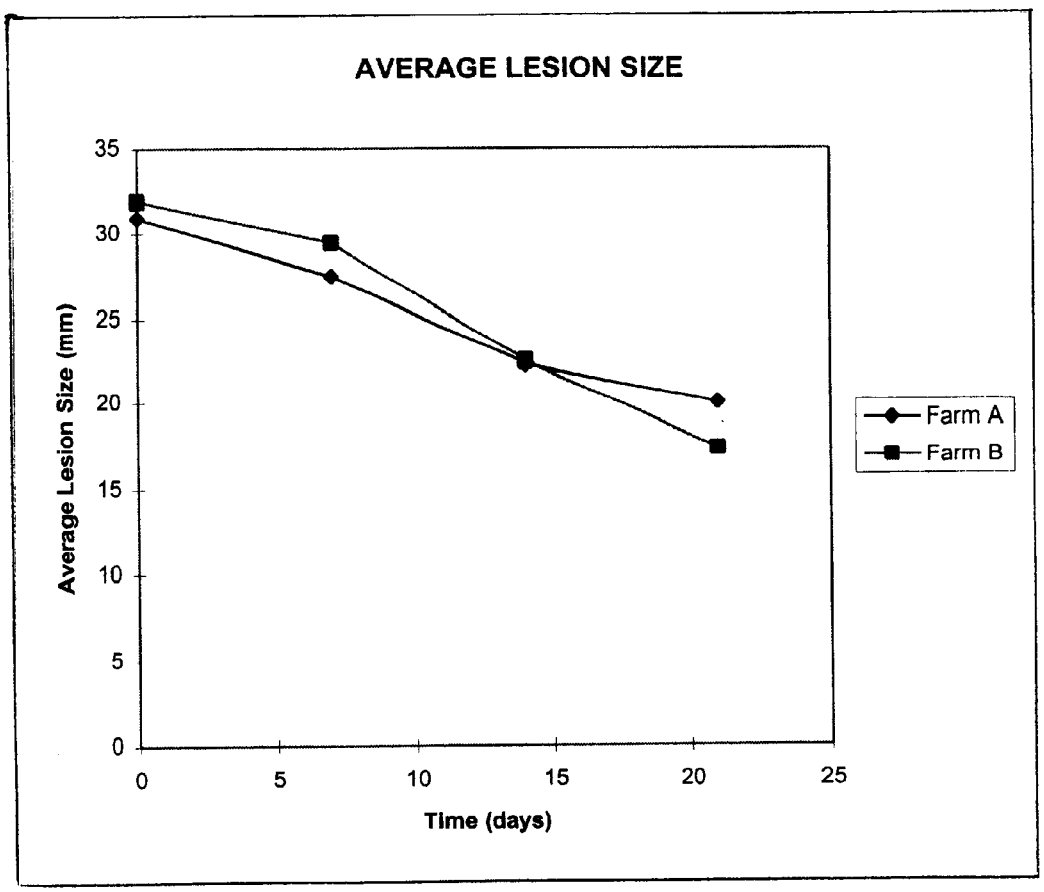
FIG. 3 is a graph depicting the change in the size of lesions on PDD-infected cattle treated with a composition according to the invention.
Figure 4:
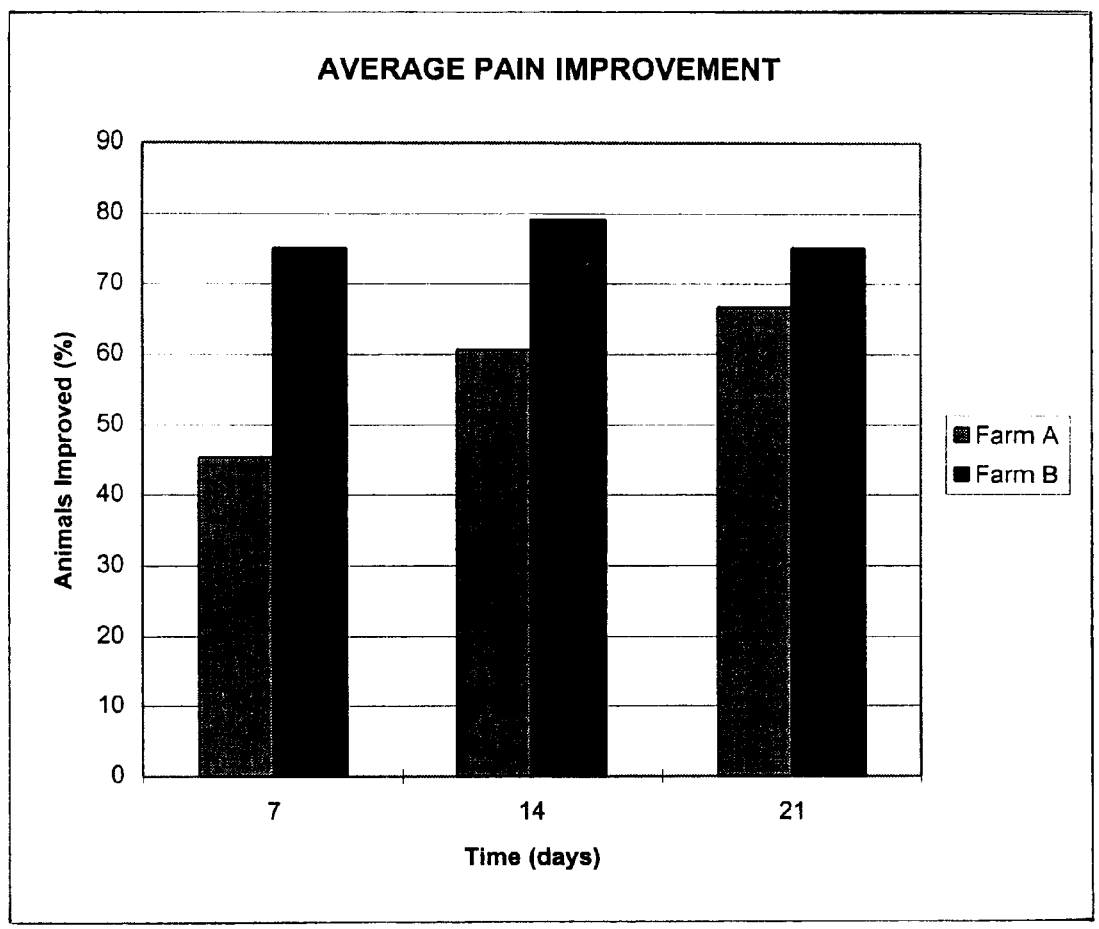
FIG. 4 is a graph depicting the percentage of PDD-infected cattle who had decreased pain after treatment with a composition according to the invention.
Figure 5:
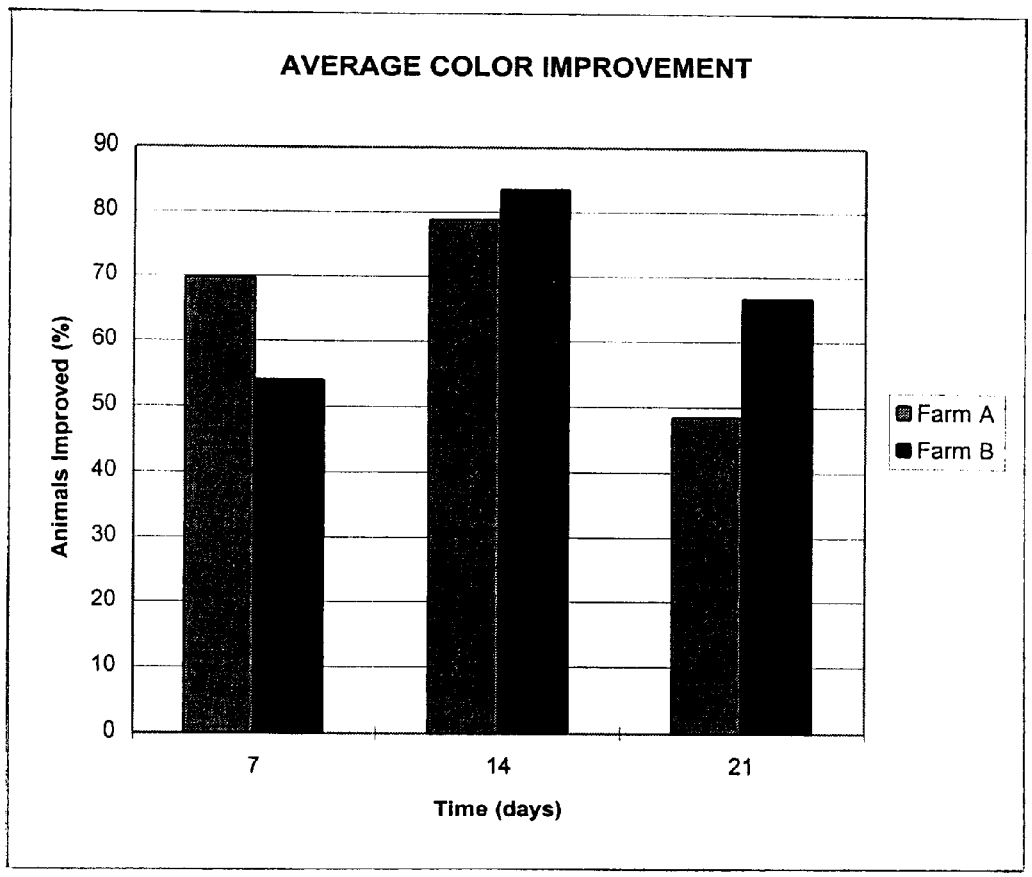
FIG. 5 is a graph depicting the percentage of PDD-infected cattle who had improved lesion color after treatment with a composition according to the invention.
Figure 6:
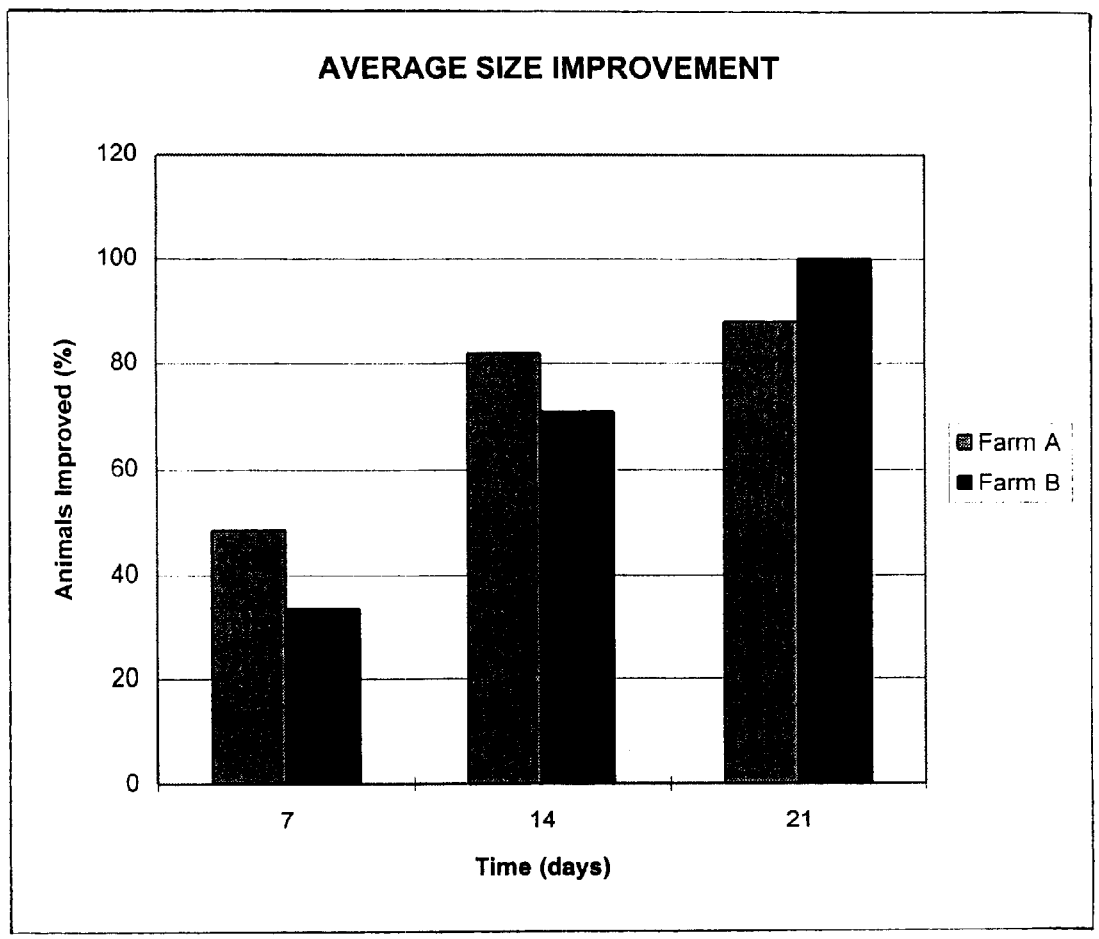
FIG. 6 is a graph depicting the percentage of PDD-infected cattle who had decrease in lesion size after treatment with a composition according to the invention.

The pain, lesion color, and lesion size data of Farm A are reported in Tables 5, 6, and 7, respectively while the pain, lesion color, and lesion size data of Farm B are reported in Tables 8, 9, and 10, respectively. The average pain scores, lesion colors, and lesion sizes are depicted in FIGS. 1–3, respectively. The percent of animals improved after treatment in pain, lesion color, and lesion size are depicted in FIGS. 4–6, respectively. An animal was considered to be improved in pain if its pain score decreased by one full point. Similarly, an animal was considered to be improved in lesion color if its lesion color score decreased by one full point. Finally, an animal was considered to be improved in lesion size if the lesion size decreased by at least 5 mm.

TABLE 5

| | | | 0 = NO<br>1 = SENSITIVE | | | | | |
|---|---|---|---|---|---|---|---|---|
| | R = Right<br>L = Left | | 2 = YES<br>PAIN | | | | | I = Improved |
| Animal ID # | HOOF<br>REAR | Prior to<br>treatment | Day 7 | | Day 14 | | Day 21 | S = Same<br>W = Worsened |
| 48 | RR | 2 | 1 | I | 0 | I | 0 | I |
| 61 | LR | 2 | 1 | I | 2 | S | 2 | S |
| 90 | RR | 2 | 1 | I | 1 | I | 1 | I |
| 92 | RR | 2 | 1 | I | 1 | I | 2 | S |
| 97 | LR | 2 | 1 | I | 1 | I | 1 | I |
| 101 | RR | 1 | 1 | S | 0 | I | 0 | I |
| 102 | RR | 2 | 0 | I | 0 | I | 2 | S |
| 104 | RR | 2 | 1 | I | 1 | I | 0 | I |
| 104 | LR | 2 | 1 | I | 1 | I | 1 | I |
| 113 | RR | 2 | 0 | I | 0 | I | 0 | I |
| 120 | RR | 1 | 1 | S | 0 | I | 0 | I |
| 122 | RR | 2 | 1 | I | 0 | I | 0 | I |
| 127 | LR | 1 | 2 | W | 1 | S | 2 | W |
| 128 | RR | 2 | 2 | S | 1 | I | 1 | I |
| 133 | LR | 2 | 0 | I | 0 | I | 1 | I |
| 136 | RR | 1 | 0 | I | 1 | S | 1 | S |
| 144 | LR | 2 | 1 | I | 1 | I | 0 | I |
| 144 | RR | 2 | 1 | I | 1 | I | 0 | I |
| 175 | LR | 2 | 1 | I | 1 | I | 1 | I |
| 185 | RR | 2 | 1 | I | 1 | I | 1 | I |
| 192 | RR | 1 | 1 | S | 0 | I | 0 | I |
| 518 | RR | 2 | 1 | I | 1 | I | 0 | I |

TABLE 5-continued

| | | 0 = NO<br>1 = SENSITIVE<br>2 = YES<br>PAIN | | | | | | |
|---|---|---|---|---|---|---|---|---|
| R = Right<br>L = Left | | | | | | | | I = Improved |
| Animal ID # | HOOF<br>REAR | Prior to<br>treatment | Day 7 | | Day 14 | | Day 21 | S = Same<br>W = Worsened |
| 573 | LR | 2 | 1 | I | 2 | S | 2 | S |
| 579 | LR | 1 | 1 | S | 1 | S | 0 | I |
| Total Points | | 42 | 22 | | 18 | | 18 | |
| Average Points per Cow | | 1.8 | 0.9 | | 0.8 | | 0.8 | |
| Percent Improved | | | 75.0 | | 79.2 | | 75.0 | |
| Percent Worsened | | | 4.2 | | 0.0 | | 4.2 | |
| Percent No Change | | | 20.8 | | 20.8 | | 20.8 | |

TABLE 6

| | | 4 = RED 3 = WHITE<br>2 = GRAY 1 = BLACK<br>0 = FLESH<br>LESION COLOR | | | | | | |
|---|---|---|---|---|---|---|---|---|
| R = Right<br>L = Left | | | | | | | | I = Improved |
| Animal ID # | HOOF<br>REAR | Prior to<br>treatment | Day 7 | | Day 14 | | Day 21 | S = Same<br>W = Worsened |
| 48 | RR | 1.0 | 1.0 | S | 1.0 | S | 1.0 | S |
| 61 | LR | 3.5 | 3.0 | S | 3.0 | S | 3.5 | S |
| 90 | RR | 3.5 | 1.0 | I | 1.5 | I | 0.5 | I |
| 92 | RR | 2.0 | 1.0 | I | 3.5 | W | 4.0 | W |
| 97 | LR | 2.0 | 1.0 | I | 1.0 | I | 1.0 | I |
| 101 | RR | 2.0 | 1.0 | I | 1.0 | I | 1.5 | S |
| 102 | RR | 2.5 | 3.0 | S | 1.0 | I | 4.0 | W |
| 104 | RR | 2.5 | 2.0 | S | 1.5 | I | 1.0 | I |
| 104 | LR | 3.5 | 1.0 | I | 2.0 | I | 2.0 | I |
| 113 | RR | 3.0 | 1.0 | I | 1.0 | I | 1.0 | I |
| 120 | RR | 2.0 | 2.0 | S | 1.0 | I | 2.0 | S |
| 122 | RR | 3.0 | 2.0 | I | 2.0 | I | 1.5 | I |
| 127 | LR | 2.5 | 2.0 | S | 1.5 | I | 1.0 | I |
| 128 | RR | 4.0 | 3.0 | I | 2.0 | I | 3.5 | S |
| 133 | LR | 2.0 | 1.0 | I | 2.0 | S | 2.0 | S |
| 136 | RR | 2.0 | 1.0 | I | 1.0 | I | 1.0 | I |
| 144 | LR | 2.0 | 1.0 | I | 1.0 | I | 1.0 | I |
| 144 | RR | 2.0 | 1.0 | I | 1.0 | I | 1.0 | I |
| 175 | LR | 2.0 | 1.0 | I | 1.0 | I | 1.0 | I |
| 185 | RR | 2.5 | 4.0 | W | 1.5 | I | 1.5 | I |
| 192 | RR | 3.0 | 3.0 | S | 0.0 | I | 0.0 | I |
| 518 | RR | 2.0 | 2.0 | S | 1.0 | I | 1.0 | I |
| 573 | LR | 3.5 | 3.5 | S | 1.0 | I | 2.0 | I |
| 579 | LR | 3.0 | 4.0 | W | 1.0 | I | 1.0 | I |
| Total Points | | 61 | 46 | | 34 | | 39 | |
| Average Points per Cow | | 2.5 | 1.9 | | 1.4 | | 1.6 | |
| Percent Improved | | | 54.2 | | 83.3 | | 66.7 | |
| Percent Worsened | | | 8.3 | | 4.2 | | 8.3 | |
| Percent No Change | | | 37.5 | | 12.5 | | 25.0 | |

TABLE 7

| Animal ID # | R = Right<br>L = Left<br>HOOF<br>REAR | LESION SIZE (in mm) | | | | | | | I = Improved<br>S = Same<br>W = Worsened |
|---|---|---|---|---|---|---|---|---|---|
| | | Prior to<br>treatment | Day 7 | | Day 14 | | Day 21 | | |
| 48 | RR | 32 | 30 | S | 20 | I | 15 | | I |
| 61 | LR | 40 | 40 | S | 35 | I | 35 | | I |
| 90 | RR | 55 | 60 | W | 25 | I | 30 | | I |
| 92 | RR | 25 | 25 | S | 12 | I | 10 | | I |
| 97 | LR | 22 | 30 | W | 20 | S | 15 | | I |
| 101 | RR | 20 | 20 | S | 15 | I | 10 | | I |
| 102 | RR | 20 | 22 | S | 25 | W | 10 | | I |
| 104 | RR | 60 | 40 | I | 20 | I | 15 | | I |
| 104 | LR | 20 | 20 | S | 25 | W | 10 | | I |
| 113 | RR | 22 | 20 | S | 15 | I | 10 | | I |
| 120 | RR | 25 | 20 | I | 20 | I | 7 | | I |
| 122 | RR | 25 | 25 | S | 25 | S | 10 | | I |
| 127 | LR | 35 | 30 | I | 20 | I | 20 | | I |
| 128 | RR | 20 | 20 | S | 20 | S | 15 | | I |
| 133 | LR | 25 | 30 | W | 25 | S | 10 | | I |
| 136 | RR | 35 | 30 | I | 30 | I | 25 | | I |
| 144 | LR | 35 | 30 | I | 30 | I | 30 | | I |
| 144 | RR | 40 | 40 | S | 30 | I | 35 | | I |
| 175 | LR | 40 | 25 | I | 20 | I | 20 | | I |
| 185 | RR | 35 | 35 | S | 35 | S | 30 | | I |
| 192 | RR | 25 | 20 | I | 0 | I | 0 | | I |
| 518 | RR | 25 | 25 | S | 20 | I | 5 | | I |
| 573 | LR | 40 | 40 | S | 25 | I | 25 | | I |
| 579 | LR | 45 | 30 | I | 27 | I | 25 | | I |
| Total Points | | 766 | 707 | | 539 | | 417 | | |
| Average Points<br>per Cow | | 31.9 | 29.5 | | 22.5 | | 17.4 | | |
| Percent<br>Improved | | | 33.3 | | 70.8 | | 100.0 | | |
| Percent<br>Worsened | | | 12.5 | | 8.3 | | 0.0 | | |
| Percent No<br>Change | | | 54.2 | | 20.8 | | 0.0 | | |

TABLE 8

| Animal ID # | R = Right<br>L = Left<br>HOOF<br>REAR | 2 = YES<br>1 = SENSITIVE<br>0 = NO<br>PAIN | | | | | | | I = Improved<br>S = Same<br>W = Worsened |
|---|---|---|---|---|---|---|---|---|---|
| | | Prior to<br>Treatment | Day 7 | | Day 15 | | Day 20 | | |
| 21 | RR | 2 | 2 | S | 0 | I | 0 | | I |
| 80 | RR | 1 | 1 | S | 1 | S | 1 | | S |
| 80 | LR | 2 | 1 | I | 1 | I | 1 | | I |
| 84 | RR | 2 | 2 | S | 2 | S | 0 | | I |
| 140 | RR | 2 | 1 | I | 1 | I | 0 | | I |
| 166 | RR | 1 | 2 | W | 1 | S | 2 | | W |
| 172 | LR | 2 | 1 | I | 1 | I | 0 | | I |
| 180 | RR | 2 | 2 | S | 2 | S | 2 | | S |
| 187 | RR | 2 | 1 | I | 0 | I | 0 | | I |
| 188 | RR | 2 | 1 | I | 1 | I | 1 | | I |
| 191 | RR | 2 | 1 | I | 2 | S | 1 | | I |
| 285 | LR | 2 | 1 | I | 1 | I | 1 | | I |
| 285 | RR | 2 | 1 | I | 1 | I | 1 | | I |
| 290 | RR | 2 | 1 | I | 0 | I | 0 | | I |
| 915 | RR | 2 | 1 | I | 1 | I | 2 | | S |
| 945 | RR | 2 | 1 | I | 1 | I | 0 | | I |
| 961 | RR | 2 | 1 | I | 1 | I | 2 | | S |
| 1021 | RR | 2 | 0 | I | 1 | I | 1 | | I |
| 1024 | LR | 2 | 1 | I | 2 | S | 1 | | I |
| 1027 | RR | 2 | 2 | S | 2 | S | 2 | | S |
| 1029 | LR | 2 | 2 | S | 2 | S | 2 | | S |
| 1031 | RR | 2 | 2 | S | 2 | S | 2 | | S |
| 1046 | RR | 2 | 1 | I | 1 | I | 1 | | I |
| 1048 | LR | 2 | 2 | S | 2 | S | 0 | | I |
| 1134 | RR | 2 | 2 | S | 2 | S | 2 | | S |

TABLE 8-continued

| | | 2 = YES<br>1 = SENSITIVE<br>0 = NO<br>PAIN | | | | | | |
|---|---|---|---|---|---|---|---|---|
| | R = Right<br>L = Left | | | | | | | I = Improved |
| Animal ID # | HOOF REAR | Prior to Treatment | Day 7 | | Day 15 | | Day 20 | S = Same<br>W = Worsened |
| 1138 | RR | 2 | 2 | S | 1 | I | 1 | I |
| 1138 | LR | 2 | 2 | S | 1 | I | 1 | I |
| 1139 | LR | 2 | 2 | S | 2 | S | 1 | I |
| 1140 | LR | 2 | 2 | S | 2 | S | 0 | I |
| 3082 | LR | 2 | 2 | S | 1 | I | 0 | I |
| 3189 | RR | 2 | 2 | S | 1 | I | 2 | S |
| 4102 | RR | 2 | 2 | S | 0 | I | 2 | S |
| 4102 | LR | 2 | 2 | S | 1 | I | 1 | I |
| Total Points | | 64 | 49 | | 40 | | 33 | |
| Average Points per Cow | | 1.9 | 1.5 | | 1.2 | | 1.0 | |
| Percent Improved | | | 45.5 | | 60.6 | | 66.7 | |
| Percent Worsened | | | 3.0 | | 0.0 | | 3.0 | |
| Percent No Change | | | 51.5 | | 39.4 | | 30.3 | |

TABLE 9

| | | 4 = RED 3 = WHITE<br>2 = GRAY 1 = BLACK<br>0 = FLESH<br>LESION COLOR | | | | | | |
|---|---|---|---|---|---|---|---|---|
| | R = Right<br>L = Left | | | | | | | I = Improved |
| Animal ID # | HOOF REAR | Prior to treatment | Day 7 | | Day 15 | | Day 20 | S = Same<br>W = Worsened |
| 21 | RR | 3.0 | 1.0 | I | 2.0 | I | 1.0 | I |
| 80 | RR | 3.0 | 1.5 | I | 2.0 | I | 1.0 | I |
| 80 | LR | 3.0 | 1.0 | I | 2.0 | I | 1.0 | I |
| 84 | RR | 2.0 | 1.5 | S | 1.0 | I | 2.0 | S |
| 140 | RR | 3.0 | 1.0 | I | 2.0 | I | 3.0 | S |
| 166 | RR | 2.0 | 3.0 | W | 0.0 | I | 3.5 | W |
| 172 | LR | 3.5 | 1.5 | I | 2.0 | I | 2.0 | I |
| 180 | RR | 3.5 | 3.5 | S | 3.5 | S | 3.5 | S |
| 187 | RR | 3.0 | 2.0 | I | 1.0 | I | 1.5 | I |
| 188 | RR | 3.0 | 1.5 | I | 1.5 | I | 1.5 | I |
| 191 | RR | 3.5 | 2.0 | I | 1.5 | I | 1.5 | I |
| 285 | LR | 3.5 | 1.5 | I | 1.5 | I | 2.0 | I |
| 285 | RR | 3.5 | 2.0 | I | 1.5 | I | 1.5 | I |
| 290 | RR | 3.5 | 1.0 | I | 1.0 | I | 3.0 | S |
| 915 | RR | 3.5 | 1.0 | I | 1.0 | I | 3.5 | S |
| 945 | RR | 3.5 | 1.0 | I | 1.0 | I | 0.0 | I |
| 961 | RR | 3.5 | 2.5 | I | 2.0 | I | 3.5 | S |
| 1021 | RR | 3.0 | 1.0 | I | 1.0 | I | 1.0 | I |
| 1024 | LR | 3.5 | 3.5 | S | 2.0 | I | 2.0 | I |
| 1027 | RR | 3.5 | 3.5 | S | 3.5 | S | 3.5 | S |
| 1029 | LR | 3.5 | 3.0 | S | 3.0 | S | 3.5 | S |
| 1031 | RR | 3.5 | 2.7 | S | 3.5 | S | 3.5 | S |
| 1046 | RR | 3.5 | 2.0 | I | 1.5 | I | 1.0 | I |
| 1048 | LR | 3.5 | 2.0 | I | 0.0 | I | 0.0 | I |
| 1134 | RR | 3.5 | 2.0 | I | 2.0 | I | 3.5 | S |
| 1138 | RR | 3.0 | 2.0 | I | 3.0 | S | 2.3 | S |
| 1138 | LR | 2.5 | 1.5 | I | 1.0 | I | 2.0 | S |
| 1139 | LR | 3.0 | 1.5 | I | 3.0 | S | 3.0 | S |
| 1140 | LR | 3.0 | 1.5 | I | 1.0 | I | 1.0 | I |
| 3082 | LR | 3.5 | 1.5 | I | 3.5 | S | 3.5 | S |
| 3189 | RR | 3.0 | 3.5 | S | 2.0 | I | 3.5 | S |
| 4102 | RR | 2.0 | 2.0 | S | 1.0 | I | 2.0 | S |
| 4102 | LR | 3.5 | 3.0 | S | 1.5 | I | 2.0 | I |
| Total Points | | 105 | 65 | | 59 | | 72 | |
| Average Points per Cow | | 3.2 | 2.0 | | 1.8 | | 2.2 | |
| Percent Improved | | | 69.7 | | 78.8 | | 48.5 | |

TABLE 9-continued

| Animal ID # | R = Right<br>L = Left<br>HOOF<br>REAR | Prior to<br>treatment | 4 = RED 3 = WHITE<br>2 = GRAY 1 = BLACK<br>0 = FLESH<br>LESION COLOR<br>Day 7 | Day 15 | Day 20 | I = Improved<br>S = Same<br>W = Worsened |
|---|---|---|---|---|---|---|
| Percent Worsened | | | 3.0 | 0.0 | 3.0 | |
| Percent No Change | | | 27.3 | 21.2 | 48.5 | |

TABLE 10

| Animal ID # | R = Right<br>L = Left<br>HOOF<br>REAR | Prior to<br>treatment | LESION SIZE (in mm)<br>Day 7 | | Day 15 | | Day 20 | I = Improved<br>S = Same<br>W = Worsened |
|---|---|---|---|---|---|---|---|---|
| 21 | RR | 35 | 30 | I | 25 | I | 25 | I |
| 80 | RR | 25 | 25 | S | 15 | I | 15 | I |
| 80 | LR | 25 | 22 | S | 20 | I | 15 | I |
| 84 | RR | 20 | 25 | W | 25 | W | 20 | S |
| 140 | RR | 25 | 25 | S | 20 | I | 20 | I |
| 166 | RR | 25 | 25 | S | 15 | I | 15 | I |
| 172 | LR | 30 | 25 | I | 20 | I | 20 | I |
| 180 | RR | 20 | 25 | W | 20 | S | 20 | S |
| 187 | RR | 30 | 20 | I | 10 | I | 10 | I |
| 188 | RR | 30 | 30 | S | 30 | S | 25 | I |
| 191 | RR | 35 | 30 | I | 25 | I | 25 | I |
| 285 | LR | 30 | 35 | W | 30 | S | 25 | I |
| 285 | RR | 40 | 30 | I | 30 | I | 30 | I |
| 290 | RR | 25 | 25 | S | 15 | I | 15 | I |
| 915 | RR | 30 | 30 | S | 25 | I | 20 | I |
| 945 | RR | 20 | 25 | W | 10 | I | 0 | I |
| 961 | RR | 30 | 25 | I | 25 | I | 20 | I |
| 1021 | RR | 40 | 35 | I | 30 | I | 20 | I |
| 1024 | LR | 30 | 25 | I | 15 | I | 20 | I |
| 1027 | RR | 40 | 25 | I | 30 | I | 25 | I |
| 1029 | LR | 40 | 25 | I | 30 | I | 25 | I |
| 1031 | RR | 45 | 30 | I | 25 | I | 30 | I |
| 1046 | RR | 30 | 30 | S | 25 | I | 25 | I |
| 1048 | LR | 20 | 20 | S | 0 | I | 0 | I |
| 1134 | RR | 25 | 30 | W | 30 | W | 25 | S |
| 1138 | RR | 50 | 35 | I | 25 | I | 30 | I |
| 1138 | LR | 35 | 30 | I | 25 | I | 25 | I |
| 1139 | LR | 20 | 20 | S | 20 | S | 20 | I |
| 1140 | LR | 30 | 30 | S | 25 | I | 20 | I |
| 3082 | LR | 35 | 30 | I | 25 | I | 20 | I |
| 3189 | RR | 30 | 20 | I | 10 | I | 10 | I |
| 4102 | RR | 40 | 35 | I | 30 | I | 25 | I |
| 4102 | LR | 35 | 35 | S | 30 | I | 20 | I |
| Total Points | | 1020 | 907 | | 735 | | 660 | |
| Average Points per Cow | | 30.9 | 27.5 | | 22.3 | | 20.0 | |
| Percent Improved | | | 48.5 | | 81.8 | | 87.9 | |
| Percent Worsened | | | 15.2 | | 6.1 | | 0.0 | |
| Percent No Change | | | 36.4 | | 12.1 | | 12.1 | |

We claim:

1. An aqueous concentrate useful for treating or preventing hoof diseases in bovines, said concentrate consisting essentially of a quaternary ammonium compound, an acid, and a surfactant.

2. The concentrate of claim 1, wherein said quaternary ammonium compound is selected from the group consisting of alkyl dimethyl benzyl ammonium salts, alkyl dimethyl ethyl benzyl ammonium salts, dialkyl dimethyl ammonium salts, dialkyl methyl benzyl ammonium salts, and mixtures thereof.

3. The concentrate of claim 2, wherein said quaternary ammonium compound is selected from the group consisting of N-alkyl dimethyl benzyl ammonium chloride, octyl decyl dimethyl ammonium chloride, dioctyl dimethyl ammonium chloride, didecyl dimethyl ammonium chloride, and mixtures thereof.

4. The concentrate of claim 1, wherein said quaternary ammonium compound is present in said concentrate at a level of from about 1–30% by weight, based upon the total weight of the concentrate taken as 100% by weight.

5. The concentrate of claim 1, wherein said surfactant is selected from the group consisting of amphoteric surfactants, nonionic surfactants, and mixtures thereof.

6. The concentrate of claim 5, wherein said surfactant is selected from the group consisting of imidazolines, betaines, alkyl phenol or alcohol ethoxylates, ethylene oxide propylene oxide adducts, and mixtures thereof.

7. The concentrate of claim 1, wherein said surfactant is present in said concentrate at a level of from about 1–30% by weight, based upon the total weight of the concentrate taken as 100% by weight.

8. The concentrate of claim 1, wherein the pH of said concentrate is less than about 4.

9. The concentrate of claim 8, wherein the pH of said concentrate is less than about 2.

10. The concentrate of claim 1, wherein said acid is selected from the group consisting of glycolic acid, citric acid, lactic acid, phosphoric acid, hydrochloric acid, sulfuric acid, acetic acid, formic acid, nitric acid, and mixtures thereof.

11. The concentrate of claim 1, said concentrate further comprising an ingredient selected from the group consisting of coloring agents, exfoliants, buffering agents, thickening agents, and mixtures thereof.

12. A method of preventing or treating a bovine hoof infected with a disease or of preventing a disease from infecting a bovine hoof, said method comprising the step of applying an effective amount of the concentrate of claim 1 to the hoof.

13. A method of preventing or treating a bovine hoof infected with a disease or of preventing a disease from infecting a bovine hoof, said method comprising the step of applying to the hoof an effective amount of a use composition comprising the concentrate of claim 1 diluted with water.

14. The method of claim 13, wherein said disease is papillomatous digital dermatitis.

15. The method of claim 13, wherein said quaternary ammonium compound is selected from the group consisting of alkyl dimethyl benzyl ammonium salts, alkyl dimethyl ethyl benzyl ammonium salts, dialkyl dimethyl ammonium salts, dialkyl methyl benzyl ammonium salts, and mixtures thereof.

16. The method of claim 15, wherein said quaternary ammonium compound is selected from the group consisting of N-alkyl dimethyl benzyl ammonium chloride, octyl decyl dimethyl ammonium chloride, dioctyl dimethyl ammonium chloride, didecyl dimethyl ammonium chloride, and mixtures thereof.

17. The method of claim 13, wherein said quaternary ammonium compound is present in said concentrate at a level of from about 1–30% by weight, based upon the total weight of the concentrate taken as 100% by weight.

18. The method of claim 13, wherein said surfactant is selected from the group consisting of amphoteric surfactants, nonionic surfactants, and mixtures thereof.

19. The method of claim 18, wherein said surfactant is selected from the group consisting of imidazolines, betaines, alkyl phenol or alcohol ethoxylates, ethylene oxide propylene oxide adducts, and mixtures thereof.

20. The method of claim 13, wherein said surfactant is present in said concentrate at a level of from about 1–30% by weight, based upon the total weight of the concentrate taken as 100% by weight.

21. The method of claim 13, wherein the pH of said concentrate is less than about 4.

22. The method of claim 21, wherein the pH of said concentrate is less than about 2.

23. The method of claim 13, wherein said acid is selected from the group consisting of glycolic acid, citric acid, lactic acid, phosphoric acid, hydrochloric acid, sulfuric acid, acetic acid, formic acid, nitric acid, and mixtures thereof.

24. The method of claim 13, said concentrate further comprising an ingredient selected from the group consisting of coloring agents, exfoliants, buffering agents, thickening agents, and mixtures thereof.

25. The method of claim 13, wherein said applying step comprises spraying said composition on said hoof.

26. The method of claim 25, wherein said use composition comprises from about 0.5–25% by volume of said concentrate.

27. The method of claim 25, wherein said applying step comprises spraying said use composition on said hoof at least about three times over the course of about one week.

28. The method of claim 13, wherein said applying step comprises applying said use composition to a piece of cloth, cotton, or other absorbent material and securing said piece to said hoof.

29. The method of claim 28, wherein said use composition comprises from about 0.5–25% by volume of said concentrate.

30. The method of claim 28, wherein said piece of cloth, cotton, or other absorbent material is maintained on said hoof for at least about 24 hours.

31. The method of claim 13, wherein said applying step comprises submerging said hoof in said use composition.

32. The method of claim 31, wherein said use composition comprises from about 0.5–25% by volume of said concentrate.

\* \* \* \* \*